United States Patent [19]

Clements

[11] Patent Number: 4,914,962

[45] Date of Patent: Apr. 10, 1990

[54] VIBRATING STRIP TRANSDUCER

[75] Inventor: David J. Clements, Sussex, England

[73] Assignee: The Slope Indicator Co., Seattle, Wash.

[21] Appl. No.: 250,157

[22] Filed: Sep. 28, 1988

[51] Int. Cl.[4] .......................... G01L 1/10; G01N 9/08; G01F 23/30

[52] U.S. Cl. .................................. 73/862.59; 73/309; 73/437

[58] Field of Search ............. 73/862.59, 309, 517 AV, 73/DIG. 1, 437, 451, 452, 453, 382, 704, 778; 177/210 FP

[56] References Cited

U.S. PATENT DOCUMENTS

| | | | |
|---|---|---|---|
| 633,471 | 9/1899 | McGarvey | 73/862.59 X |
| 2,513,678 | 7/1950 | Rieber | 73/862.59 |
| 3,071,971 | 1/1963 | Wallace | 73/451 |
| 3,216,260 | 11/1965 | Erdely | . |
| 3,411,347 | 11/1968 | Wirth et al. | 73/862.59 |
| 4,170,897 | 10/1978 | Babcock | . |
| 4,277,973 | 7/1981 | Hawkes | . |
| 4,299,122 | 11/1981 | Ueda et al. | 73/862.59 |
| 4,418,774 | 12/1983 | Whitney et al. | 177/210 FP |
| 4,476,725 | 10/1984 | Chorel et al. | . |
| 4,479,391 | 10/1984 | Banik et al. | 73/862.59 |
| 4,498,344 | 2/1985 | Dinger | . |
| 4,587,853 | 5/1986 | Komoto et al. | 73/862.59 |
| 4,703,216 | 10/1987 | Corbett | . |

FOREIGN PATENT DOCUMENTS

| | | |
|---|---|---|
| 2448750 | 9/1975 | Fed. Rep. of Germany . |
| 2732052 | 2/1979 | Fed. Rep. of Germany ...... 177/210 FP |
| 224169 | 6/1985 | Fed. Rep. of Germany . |
| 717334 | 2/1980 | U.S.S.R. . |
| 836538 | 6/1981 | U.S.S.R. . |
| 1281941 | 1/1987 | U.S.S.R. . |
| 671392 | 5/1952 | United Kingdom .................. 73/382 |
| 1068153 | 5/1967 | United Kingdom . |
| 1068154 | 5/1967 | United Kingdom . |

OTHER PUBLICATIONS

L. A. Gubarenko, "String Gravimeters", *Earth Physics*, No. 11, 1970, pp. 49–56.

"Protection of Vibrating Wire Surface Strain Gauges", by C. Beales and D. W. Cullington, Strain, vol. 11, No. 1, Jan., 1975, pp. 7–9.

"Frequency Analog Measurement Technique: Linear Displacement Transducing by Means of a vibrating String", Dominique Bouts and Theodor Gast, Technisches Messen atm, Apr., 1977, vol. 44, pp. 125–130.

"Norwegian Practice in Instrumenting Dams", by K. Y. Nilsen, E. DiBiagio and A. Andresen.

Nordic Hydrology, 16, 1985, pp. 193–202 (abstract only), "An Automatic Precipitation Gauge Based on Vibrating-Wire Strain Gauges".

Geonor T-200 Nedbormaler Pamphlet.

*Primary Examiner*—Charles A. Ruehl
*Attorney, Agent, or Firm*—Patrick M. Dwyer; David L. Garrison

[57] ABSTRACT

A vibrating strip transducer, wherein a vibrating strip 54 mounted between a fixed mount 52 and a moveable mount 51 and under load 53 directly responds to a change in force applied to the strip with a change in the magnitude of stress in the strip. The change in stress produces a corresponding change in the resonant frequency of vibrating strip 54 which is detected by coil assembly 55 to output a frequency based signal directly related to the force applied. Fluid level and buoyancy sensing embodiments are also disclosed.

13 Claims, 2 Drawing Sheets

VIBRATING STRIP TRANSDUCER

TECHNICAL FIELD

This invention relates to the field of force sensing and measuring devices. More particularly the invention relates to transducers employed to directly measure the magnitude of a force by applying the force directly to a vibrating elastic member to thereby cause changes in the resonant vibrating frequency of the vibrating member through changes in the stress in the member.

BACKGROUND OF THE INVENTION

Conventional force sensing transducers generally accommodate the applied force by means separate from those associated with a generation of the related electrical signal output. A variety of known transducers have been employed to detect and measure a variety of forces, each transducer producing an output signal roughly proportioned to the force measured. Many of the known transducers encounter problems of nonlinearity within the range of expected measurement values because what they measure is not in fact the direct effect of the force upon the output generating means. In most cases the force must first act on some other component or system within the transducer, or related to the environment in which the transducer, is placed, before there is any effect at all on the electrical signal generating means.

Some force sensing transducers employ a prestressed vibrating wire type strain gauge to create a frequency based output proportional to the stress in the vibrating wire. Prestressed wire type transducers exhibit one significant advantage over other types of force sensing transducers in that their electrical output signal format is frequency rather than analog magnitude related, and as such is largely insensitive to cable leakage, resistivity changes, etc. As a result of this attribute the reading of such instruments over several kilometers of cable is possible without downgrading of accuracy. For this reason the vibrating wire type of device is favored in the hostile environment of civil engineering applications particularly with regard to foundations and earthworks. However the prestressed vibrating wire device discussed above inherently suffers certain limitations which over the life of the installed, and often irrecoverable, transducer can and has raised doubts in users regarding the long-term stability of such units. One of the potential problems relates to long-term creep or loss of tension in the wire, whereby with time the stress level in this prestressed component decreases independent of applied force, and thus lowers the wire's resonant frequency.

Since this type of transducer, as discussed above, senses applied force as a relief of tension in the prestressed wire which reduces the resonant vibrating frequency of the wire, and since reduced frequency is usually indicative of increased applied force, such a long term decrease in wire stress, and hence resonant frequency is taken by the user to be an increase in applied force, whereas in reality all readings subsequent to tension loss are in error by the unknown extent of this tension loss.

The dimensions of this potential limitation can be illustrated by considering a typical vibrating wire pressure transducer with the following characteristics:

Range = 0–100 psi
Diameter of wire = 0.009 inch
Length of wire = 1.5 inch
Frequency output range = $4000 \times f^2/1000$ digits
where $f^2/1000$ refers to a preferred readout mode wherein $f^2$ is the square of the vibrational frequency and $f^2/1000$ is a single unit for readout purposes. In such a case, wire prestressing during assembly will stretch it by about 3 thousandths of an inch to achieve the zero applied pressure frequency of about 3000 Hz (9000 $f^2/1000$ indicated reading).

As the unit is externally loaded to full range pressure (100 psi) the pretensioned wire stress will reduce as the diaphragm strains to the applied pressure. This equates to approximately 1.2 thousandths of an inch strain over the free wire length, and as such represents the response over the full operating range of the transducer.

In terms of strain therefore, only one hundredth part 0.0012 inch, or 0.000012 inch component creep, in the diaphragm, body, wire or wire gripping points is necessary to produce an offset in frequency equivalent to 1% transducer zero drift. In terms of wire stress, only 0.4% of loss in wire prestress is necessary to cause a 1% transducer zero drift. In most civil engineering applications this cannot be detected or quantified after the unit is irretrievably installed for use.

As with most established types of force sensing transducers employing strain measuring elements separate from force absorbing components, the prestressed vibrating wire device design discussed above requires special attention to be paid to the relatively different temperature coefficient factors of the various components, in order to minimize performance changes which occur where the temperature effects on the various components do not match the effects on the prestressed wire.

Where temperature effects do not match, differential expansion or contraction occurs and causes output frequency changes to occur which cannot be differentiated from real applied force variations. This is so even in cases where there are careful design efforts to select the correct proportion of different materials to match the temperature response over a certain range of temperatures, because all components are not necessarily at the same temperature at any given time.

Temperature gradients across the various components, as the influencing temperature changes, will cause significant though transient errors in the magnitude of applied force indicated. This factor is usually of greatest significance at the time of installation where the instrument is often subjected to changes of temperature environment as placement occurs, and on such occasions the registering of erroneous datum readings before temperature stabilization occurs is not uncommon.

Other known force sensing transducers employ a relatively unstressed vibrating wire instead of a prestressed wire where the force to be measured is applied directly to the wire. However even though some of the difficulties discussed above are avoided by employing a wire which is not prestressed, devices employing hard musical wire still experience wire creep and crimp slippage even under relatively low stress levels. That is because hard steel wire must be crimped or swaged under extremely high stress levels in order to ensure gripping of the wire at the highest anticipated stress level. Under these extremely high stress levels stress is inevitably transferred longitudinally into the wire causing unavoidable wire deformations with the resulting problems as discussed above. Moreover the high stress levels force the crimp itself into plasticity, with the eventual result over time of wire slippage in the crimp resulting in the same kinds of errors discussed above for prestressed wires.

Accordingly it is an object of the invention to measure the magnitude of a force by applying it directly and as completely as possible to a vibrating strip which bears virtually all of the force to mechanically provide means by which a frequency related, rather than analog based, electrical output signal is derived directly from the stress in the strip.

It is another object of the invention to accommodate an applied force and generation of a related electrical signal output by one in the same means.

It is a further object of the invention to significantly minimize the effect of long-term creep or tension loss discussed above by employing material such as a thin steel strip which is not prestressed.

It is a still further object of the invention to provide a vibrating strip which is inherently less sensitive to thermal expansion and to temperature gradient effects than the transducers discussed above.

It is another object of the invention to provide increased reading resolution for full rated pressure range.

It is a further object of the invention to provide an invention with a design which results in uniformity of design for a variety of applied force ranges and in low completed item wastage rates.

These and other objects of the invention are accomplished according to the disclosure of the invention herein described as more fully set forth below.

DISCLOSURE OF THE INVENTION

The invention comprises a broadly applicable force sensing transducer scheme wherein a thin metal strip is fastened between two mounts, one of which is rigid and the other of which is free to move, if only to some small degree, and to which a load or force to be measured is applied. In a preferred embodiment of the broad general scheme, well known coil excitation means are used to excite the thin metal strip to vibration at its resonant frequency for a given stress level within the strip. This resonant frequency changes in proportion to the change in stress in the strip as the load in the movable mount experiences changes in the intensity of applied force. The advantages of employing a thin metal strip over a conventional wire, prestressed or not, is that even a very thin metal strip will typically have more cross-sectional area than a wire and therefore be more robust and not as susceptible to damage during handling, in addition to offering more latitude in selecting range and sensitivity for a given transducer device. It will also be easier to mount and in no case will it require swaging or crimping, with the problems associated with those attaching means as discussed above. In fact in a preferred embodiment the thin metal strip is simply spot welded to the mounts. Furthermore, the thin metal strip has a better interaction with the excitation means. In a preferred embodiment, this excitation means is a magnetic coil, but other means will occur to persons of ordinary skill in the art without departing from the scope of the invention.

The purpose of the invention in a more particular embodiment is to measure fluid level by means of the precise measurement of flotation effects upon a buoyant weight set at a fixed elevation and partially immersed in the fluid, the surface level of which it is required to measure and record. Any buoyant weight can be used whose dimensional characteristics are known, but in a preferred embodiment the buoyant weight is a dimesionally stable ballasted enclosed cylinder. Other cross sectional shapes for the weight may also be employed, although weights with a relatively constant cross sectional area are preferred for ease of calculation of fluid level. The means by which such measurement is achieved is by causing the weight of the freely suspended, partially immersed, enclosed cylinder to be directly borne by a thin steel strip from which it hangs. The essential component features of the system are shown in FIG. 3 and further disclosed herein.

In a fluid level measurement embodiment the transducer unit translates any particular magnitude of load or weight suspended from it into a proportional tensile stress level within the thin steel strip. Since this elastic member is retained at its extremities, and is of virtually constant length at all magnitudes of loading within its chosen range, it will, when excited, vibrate about its centerpoint in a plane normal to its widest face at a frequency which bears relation to the stress level within it and thus to the weight or load which produced such stress.

When the unit is secured at a fixed elevation and a ballasted weight freely suspended from it, the frequency of vibration will reflect the "dry air" weight of this load. However, as the suspended weight is progressively immersed in fluid, the increasing buoyancy effect upon it will reduce the load transmitted to, and thus the tensile stress level contained within, the thin steel strip. Therefore in a situation where transducer, hanging wire and partly immersed buoyant weight are placed at constant elevation, change of fluid level around the weight will produce a corresponding change in strip tensile stress magnitude and thus frequency of vibration once excited. Frequency of electrical signal output may therefore be calibrated against fluid level elevation.

The arrangement described above has particular advantages over a conventional immersed pressure transducer measuring method where high precision is required over relatively small variations of water level. Using a transducer of the type disclosed, range and sensitivity can be readily adjusted to suit a wide range of applications, as the following example of a vibrating strip transducer having a steel strip of 0.003 inch thickness, 0.075 inch width, and 1.35 inches unsupported length demonstrates.

In weir water level measuring applications, where expected water level variations defining an instrument range do not exceed 10 inches, a practical resolution and accuracy of better than 0.002 inches of water level is achievable. In river or ground water level measuring applications, where expected water level variations do not exceed 15 feet, a practical resolution and accuracy of better than 0.02 inches of water level is achievable. These accuracies are far better than those achieveable using conventional transducer types. Greater or lesser level variations than those quoted above may also be accommodated at corresponding larger or smaller resolutions, depending on weight dimensions, materials, and extent of ballasting.

This high degree of measurement precision is due to the inherent qualities of the vibrating strip measurement concept of the invention, namely: (a) low susceptibility of the device to long term creep effects of components within the transducer; (b) low susceptibility of the device to differential expansion of dissimilar material components due to ambient temperature change; and (c) by virtue of (a), the ability to operate the transducer over a wider range of stress, and thus frequency, values without detrimental effect, and by so doing, providing practical resolutions of up to 10,000 $f^2/1000$ reading increments per range.

In a preferred embodiment, the vibrating strip is a single steel strip. However, other materials and other cross-sectional shapes, as well as multiple and levered elements, can be employed without departing from the scope of the invention, provided the cross-sectional areas and material strengths chosen for a particular transducer are adequate to withstand tensile forces greater than the maximum expected force to which the transducer is to be exposed. Overall transducer sensitivity or range may be selected or changed at will by choice of appropriate thicknesses and widths and by choice of material in the vibrating strip.

Stress in the vibrating strip, and hence resonant frequency, are not altered by either long-term creep in the transducer components or by differential thermal expansion, except to the extent of introduction by the spring rate of the hinge and the boot which are employed in a preferred embodiment, as discussed below. The small strains resulting from long-term creep or differential expansion are absorbed by hinge and boot and therefore contribute an extremely small force error which only slightly lessens the stress in the strip. The relative effect of this error is in direct proportion to the ratio of the effective spring rate of hinge and boot combined versus the stiffness or spring rate of the vibrating strip. In practice, this ratio can be several orders of magnitude; hence, the effect of strain due to long-term creep or differential thermal expansion can be made negligible.

In another embodiment, the measurement of specific gravity in liquids is accomplished as above with only two differences. (1) The device is intended for installation in tanks or vats in such a way that the hanging weight remains entirely submerged in liquid at all times when readings are required. In a typical application where average specific gravity data is required, the height of the ballasted weight unit represents a major part of the liquid depth, and the diameter of the cylindrical weight may be considerably larger than in the typical fluid level measurement application. (2) In order to achieve the greatest resolution of measurement, and to ensure the long term dimensional stability of the submerged weight, and thus prolonged system accuracy, it may be necessary to employ a relatively heavy, rigid steel construction for the submerged weight unit. To insure negative buoyancy at all specific gravities within the required measurement range, in a typical application, dry weight of the weight unit can be 65 pounds. When suitably ballasted and entirely submerged in liquid, this weight presents a safe loading stress in the strip. However, as the tank or vat is emptied of liquid, the increasing magnitude of unbuoyed hanging weight can overstress the particular strip and cause it to fail.

A preventative measure is therefore disclosed wherein a spring having the spring rate of approximately 10 lbs./inch is inserted in series with the hanging component. On installation, with the product tank or vat dry, and the weight supported by a mechanical base, or the tank floor, the transducer assembly is raised to a point where the spring begins to extend. When the transducer reading approaches an indicated 9500 $f^2/1000$ digits, representing 15.2 pounds load in the spring and on the strip sensor the transducer assembly is locked in this position. As the vat is filled with the product and buoyancy on the cylindrical weight causes its negative buoyancy to drop below 15.2 pounds, the immersed weight will float clear of its support as the spring responds to the reduced force upon it. Henceforth it will be freely suspended and once entirely submerged will cause the system to respond unhindered to changes in specific gravity of the product liquid as previously explained.

In a typical brewing industry application, specific gravity (SG) in the range of 1.000 to 1.100 is measured. A weight unit having an outside diameter of 6.25 inches and a length of 48 inches, with a total dry weight of 65 pounds is used. Buoyancy of the weight unit due to submerged volume at SG 1.000 is calculated at 53.154 pounds, less dry weight. Buoyancy due to submerged volume at SG 1.100 is 58.469 pounds, less dry weight. Thus when the weight unit is totally immersed in liquid where SG=1.100 the strip is subjected to 65.−58.469=6.531 pounds. Similarly, where SG=1.000, the strip is subjected to 11.846 pounds.

Assuming a thin steel strip 0.003 thick by 0.075 inch wide is used as the sensor, the above figures produce the following tensile stress figures in the strip: at SG=1.000, 52,649 psi; at SG=1.100, 29,027 psi. Where the transducer constant is 625 $f^2/1000$ digits per 1 per pound, these stress figures equate to the following $f^2/1000$ readout digits displaced: at SG 1.100, 7404 indicated; at SG 1.000, 4082 indicated. The system sensitivity over the range of SG 1.000 to 1.100 is therefore 3322 indicated digits, giving an extremely sensitive resolution of 0.0003 SG.

As with the fluid level measurement embodiment of the invention, for a single basic transducer, measurement range and sensitivity may be changed to suit particular requirements by merely altering the dimensions, weights and volumes of the buoyant weight unit employed. Changing the cross-section of the strip also affords considerable latitude in choosing ranges.

BEST MODE FOR CARRYING OUT THE INVENTION

Figure 1:
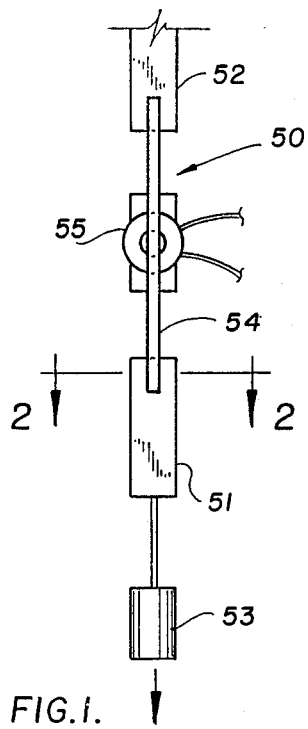
FIG. 1 is a schematic representation of a general preferred embodiment of the invention.
Figure 2:
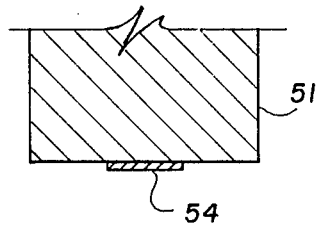
FIG. 2 is a section taken along lines 2—2 in FIG. 1.

Referring now to the drawings wherein like numbers indicate like parts a preferred embodiment of transducer 50 having broad general application is disclosed in FIGS. 1 and 2. Thin steel strip 54 is mounted between fixed mount 52 and movable mount 51. Strip 54 is excited into resonant vibration by magnetic coil assembly 55 which also generates an output signal which is frequency as opposed to analog based. Movable mount 51 may have attached to it any load 53 which may either represent the force to be measured or represents some object attached to movable mount 51 on which the force to be measured acts directly. In the preferred embodiment strip 54 is spot welded to mounts 51 and 52. This general embodiment of a vibrating strip transducer will have applications related to precise measurement of weight, acceleration and other force or gravity related parameters.

Figure 3:
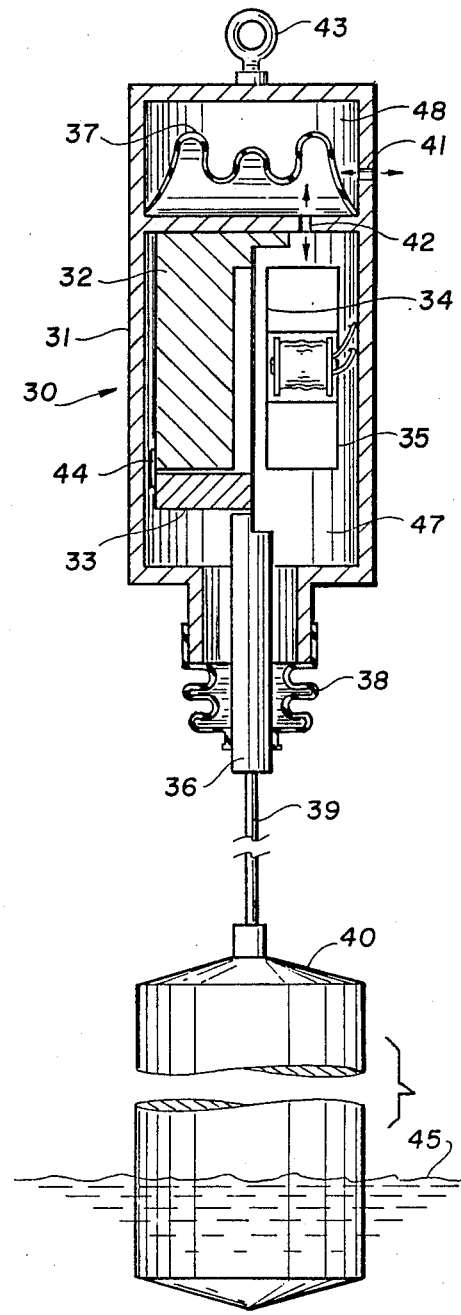
FIG. 3 is an elevational section of a fluid level sensing embodiment of the invention with hanging wire 39 and weight 40 shortened for ease of illustration.
Figure 4:
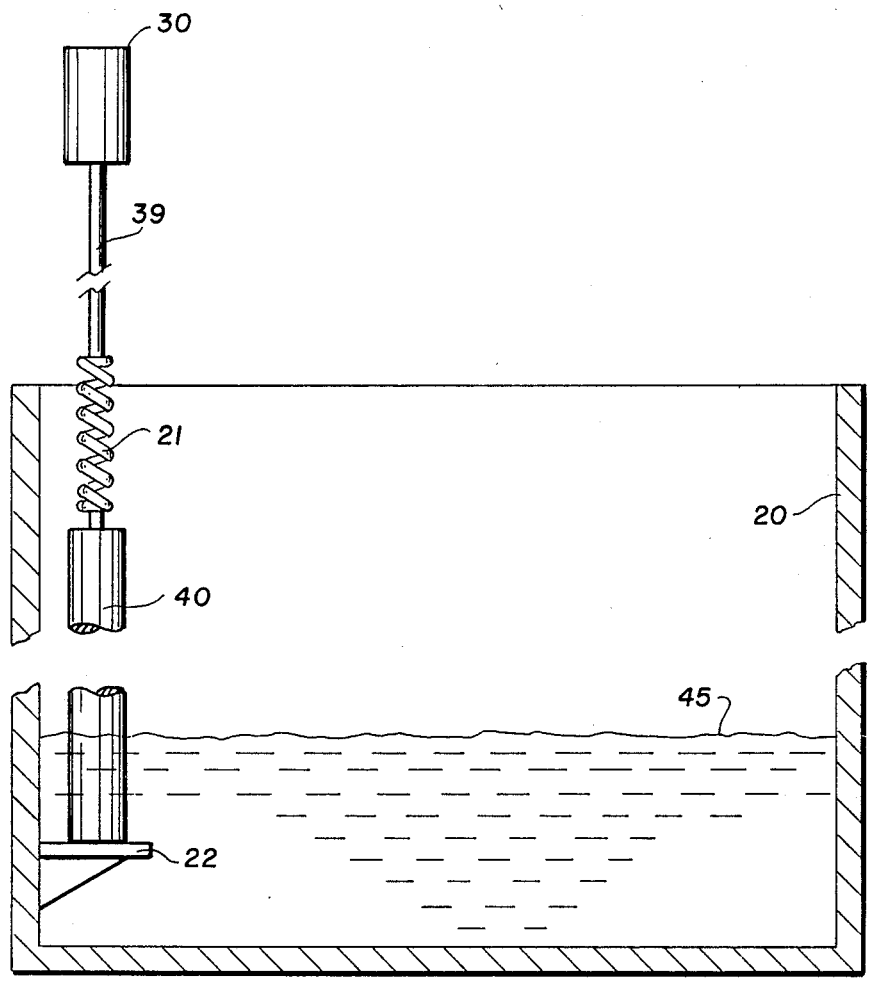
FIG. 4 is a partial sectional side elevational view of an alternative embodiment of the invention disclosed in FIG. 3.

In FIG. 3 a preferred embodiment of a fluid level or buoyancy sensing transducer is disclosed. The purpose of fluid level transducer 30 is to measure fluid level by means of precise measurement of flotation effects upon weight unit 40, which is set at a fixed elevation and partially immersed in fluid at fluid level 45. Transducer housing 31 is comprised of transducer chamber 47 and membrane chamber 48. Transducer chamber 47 is sealed against the entry of moisture by boot 38 and by membrane 37, but is retained at external barometric pressure by communicating with the volume below membrane 37 through internal port 42. Membrane 37 may be any flexible but moisture impervious membrane. In a preferred embodiment membrane 37 is a thin highly flexible plastic or rubber member. Membrane chamber 48 is divided into two compartments by membrane 37 which serve together as an ambient pressure transmitting moisture barrier. The volume above the membrane in chamber 48 communicates with atmospheric pressure through external port 41. Where entry of moisture into transducer 30 is not a critical factor, transducer chamber 47 can be vented directly to atmosphere.

Within transducer chamber 47, transducer body 32 serves as an upper mounting point for thin steel strip 34 and also as a mounting point for hinge 44 which connects body 32 with lower mount 33. Lower mount 33 provides the lower mounting point of thin steel strip 34 and also provides a mounting point for weight hanger 36. The purpose of hinge 44 on lower mount 33 is to resist the transmission of torsion and lateral displacement effects operating upon weight unit 40 that might otherwise cause damage to thin steel strip 34, and yet allow unimpeded transmission of gravitational force to strip 34 from all components hung upon hanger 36. Lower mount 33 also serves as an inertial mass to insure predictable strip vibration.

Thin steel strip 34 is suspended between an upper mounting point on transducer body 32 and lower mounting point on lower mount 33. Hence strip 34 is subjected to the aggregate weight of all other hanging components. It is thus subjected to a state of stress proportional to the applied hanging load, and is selected to have a suitable cross-section to safely withstand such force.

Coil and permanent magnet assembly 35 is secured in close proximity to strip 34 at its center line and provides the means of setting the strip into mechanical vibration at its resonant frequency and of generating from such vibration an electrical output signal of frequency based characteristics.

Hanger 36 provides a means for further connection of hanger wire 39, by which ballasted cylindrical weight unit 40 is suspended. While flexible boot 38 provides a moisture barrier, it does not significantly impede transmission to strip 34 of changes in load. Hanger wire 39 is employed to allow the transducer to be mounted at an elevation safely above maximum expected fluid level and to insure that weight 40 is set in a partially immersed position at all stages of subsequent fluid level variation.

Ballasted cylindrical weight 40 is a unit of constant diameter within the range of expected fluid level variations, and is designed to be negatively buoyant within the range of such fluid variations. Diameter, length and extent of ballasting will change dependent on the fluid level measuring range requirements. In all cases however, weight unit 40 will be dimensioned and ballasted such that at minimum fluid level its weight produces a safely born stress level on the thin steel strip 34, and such that at maximum fluid level its buoyancy is not sufficient to overcome its own weight.

With only minor changes to the embodiment shown in FIG. 3, it may also be employed to measure specific gravity in liquids. In this application the transducer 30 is installed in tanks or vats 20 in such a way that the hanging weight 40 remains entirely submerged in the liquid at all times when readings are required. When suitably ballasted and entirely submerged in liquid, this weight 40 presents a safe loading stress in the strip. However, as the tank or vat 20 is emptied of liquid, the increasing magnitude of unbuoyed hanging weight can overstress the particular strip and cause it to fall.

A preventative measure is therefore disclosed wherein a spring 21 having a spring rate of approximately 10 lbs./inch is inserted in series with the hanging component. On installation, with the product tank or vat 20 dry, and the weight supported by a mechanical base 22, or the tank floor, the transducer assembly is raised to a point where the spring 21 begins to extend. When the transducer reading approaches an indicated 9500 $f^2$/1000 digits, representing 15.2 pounds load in the spring 21 and on the strip sensor the transducer assembly 30 is locked in this position. As the vat 20 is filled with the product and buoyancy on the cylindrical weight 40 causes its negative buoyancy to drop below 15.2 pounds, the emersed weight will float clear of its support 22 as the spring 21 responds to the reduced force upon it. Henceforth it will be freely suspended and once entirely submerged will cause the system o respond unhindered to changes in specific gravity of the product liquid as previously explained.

Other changes in dimension and construction of weight unit 40 for this application, as well as modifications to hanger wire 39 to incorporate a spring 21 are as discussed above.

In both the fluid level measurement embodiment and the specific gravity measuring embodiment discussed above, measuring range and sensitivity using a single basic transducer, may be changed to suit particular requirements by merely altering the dimensions, weights, and volumes of the buoyant weight 40 employed. In addition, changing the cross-section of the strip will also afford considerable latitude in choosing ranges.

In compliance with the statute the invention has been described in language more or less specific as to structural and functional features. It is to be understood, however, that the invention is not limited to the specific features shown, since the means of construction and method herein disclosed comprise only a preferred form of putting the invention into effect. Other modifications and other variations of my apparatus and method will occur to those of ordinary skill in the art. Accordingly the foregoing description is to be interpreted in an illustrative and not in a limitative sense and the invention is claimed in any of its forms or modifications with the legitimate valid scope of the appended claims appropriately interpreted in accordance with the doctrine of equivalents.

INDUSTRIAL APPLICABILITY

The invention and its several embodiments disclosed herein will find use not only generally in the field of force sensing and measurement in a virtually limitless variety of engineering applications but particularly in the detection and measurement of buoyancy and/or fluid level. The invention will be especially useful where it is important to achieve high long-term accuracy with high linearity of response and wherever it is desirable to match the range and sensitivity of a force sensing device with the expected range of magnitudes of forces or levels to be measured. The invention will be further useful in that there will be, as a result of the method of manufacturing, a much lower rate of factory rejections and a much greater shelf life for the product. Moreover devices may be custom fabricated according to the invention by attaching an appropriately dimensioned strip with simple welding methods to match the range of forces expected for the application. In cases where a sensing device will be accessible after installation, a subsequent change in magnitude of forces or a desired change in sensitivity range of the instrument for any other reason may be accommodated by removing the strip from the device and replacing it with a different strip.

I claim:

1. A vibrating strip transducer comprising:
a body, having a substantially fixed mount; a thin metal strip attached to said fixed mount; a relatively moveable mount attached to the opposite end of said strip, said moveable mount connected to a hanger for mechanical interaction with an externally applied force; a hinge interconnecting said moveable mount and said body, said hinge for resisting transfer of twisting forces from said hanger to said strip; and an excitation means for exciting the strip into vibration at its resonant frequency and generating a frequency based signal output.

2. The apparatus of claim 1 wherein said thin metal strip is substantially rectangular in cross-section.

3. The apparatus of claim 1, further comprising: a housing, said housing enclosing said body, said fixed mount, said moveable mount, said strip and said excitation means, the interior of said housing communicating with external barometric pressure.

4. The apparatus of claim 3 wherein said housing communicates with barometric pressure across a flexible, moisture impervious membrane.

5. The apparatus of claim 4 wherein a portion of said hanger extends beyond said housing, further comprising: a flexible boot for sealing said housing around said hanger while permitting movement of said hanger.

6. The apparatus of claim 1 wherein said thin metal strip is steel.

7. An apparatus for fluid level measurement comprising, in combination (a) the apparatus of claim 1, and (b) dependent from said hanger, a buoyant weight unit dimensioned such that, at a minimum fluid level, the magnitude of the weight of said weight unit produces a stress level in said thin strip which is below the yield stress for said strip, and at a maximum fluid level, buoyancy of said weight unit is not sufficient to overcome its own weight.

8. The apparatus of claim 7 wherein said weight unit is cylindrical and has a constant diameter within the range of said minimum fluid level and said maximum fluid level.

9. An apparatus for measurement of specific gravity in a liquid comprising, in combination, (a) the apparatus of claim 1, and (b) dependent from said hanger, a weight unit having a buoyancy, when entirely submerged in said liquid, insufficient to overcome its own weight.

10. An apparatus of claim 9 wherein said weight unit is ballasted so that when entirely submerged in said liquid said weight unit presents a loading stress in said strip which is below the yield stress for said strip.

11. The apparatus of claim 10 further comprising: a support for preventing said weight unit, when not entirely submerged in said liquid, from overloading said strip.

12. The apparatus of claim 11 further comprising: a spring disposed between said hanger and said weight unit, said spring having spring rate low enough to permit said weight unit to come into contact with said support when said liquid has a liquid level which does not entirely submerge said weight unit.

13. The apparatus of claim 12 wherein said spring has a spring rate of approximately 10 lbs./inch.

* * * * *